(12) United States Patent
Lechot et al.

(10) Patent No.: US 7,600,451 B2
(45) Date of Patent: Oct. 13, 2009

(54) DETACHABLE SURGICAL RATCHET

(75) Inventors: Andre Lechot, Orvin (CH); Philippe Fehlbaum, Lignières (CH)

(73) Assignee: Greatbatch Medical SA, Orvin (CH)

( * ) Notice: Subject to any disclaimer, the term of this patent is extended or adjusted under 35 U.S.C. 154(b) by 575 days.

(21) Appl. No.: 10/554,044

(22) PCT Filed: Apr. 23, 2004

(86) PCT No.: PCT/IB2004/001244

§ 371 (c)(1),
(2), (4) Date: Oct. 20, 2005

(87) PCT Pub. No.: WO2004/096069

PCT Pub. Date: Nov. 11, 2004

(65) Prior Publication Data

US 2006/0243108 A1    Nov. 2, 2006

(51) Int. Cl.
*B25B 13/46* (2006.01)
(52) U.S. Cl. .............................. 81/62; 81/60
(58) Field of Classification Search ............. 81/60–63.2
See application file for complete search history.

(56) References Cited

U.S. PATENT DOCUMENTS

| | | | |
|---|---|---|---|
| 2,720,296 A | 10/1955 | Anton | |
| 2,867,144 A | 1/1959 | Stevens | |
| 2,893,278 A | 7/1959 | Rice | |
| 3,654,975 A | 4/1972 | Ballsmith et al. | |
| 4,157,120 A * | 6/1979 | Anderson | 173/93 |
| 4,302,990 A * | 12/1981 | Chrichton et al. | 81/60 |
| 4,382,476 A * | 5/1983 | Swenson | 173/93.5 |
| 4,466,523 A | 8/1984 | De Carolis et al. | |
| 4,529,071 A * | 7/1985 | Gagnon et al. | 192/43.1 |
| 4,727,782 A * | 3/1988 | Yang | 81/124.4 |
| 4,762,033 A * | 8/1988 | Chow | 81/63.2 |
| 5,437,212 A | 8/1995 | Thompson et al. | |
| 5,520,073 A | 5/1996 | Bakula et al. | |
| 5,535,648 A | 7/1996 | Braun et al. | |
| 5,551,323 A | 9/1996 | Beere et al. | |
| 5,613,585 A | 3/1997 | Tiede | |
| 5,619,891 A | 4/1997 | Tiede | |
| 5,622,089 A | 4/1997 | Gifford, Sr. | |
| 5,647,252 A | 7/1997 | Miner | |
| 5,738,192 A | 4/1998 | Miner | |
| 5,749,272 A | 5/1998 | Phan | |
| 5,771,760 A | 6/1998 | Tiede | |
| 5,778,743 A | 7/1998 | Tiede | |
| 5,848,680 A | 12/1998 | Rinner | |
| 5,873,288 A | 2/1999 | Gauthier et al. | |
| 5,910,196 A | 6/1999 | Huang | |
| 5,928,154 A | 7/1999 | Silber et al. | |
| 5,943,755 A | 8/1999 | Gauthier et al. | |
| 6,059,083 A | 5/2000 | Tseng | |
| 6,070,501 A * | 6/2000 | Braun et al. | 81/62 |
| 6,082,226 A | 7/2000 | Lin | |
| 6,105,770 A * | 8/2000 | Vasudeva | 206/378 |

(Continued)

*Primary Examiner*—David B Thomas
(74) *Attorney, Agent, or Firm*—Moetteli & Associates SaRL

(57) ABSTRACT

A surgical ratchet assembly includes a handle, a driver, a ratcheting mechanism and a locking mechanism. The driver is received within the handle in a rotatable relationship with respect thereto. The ratcheting mechanism is interposed between the handle and the driver. A locking mechanism releasably holds the handle to the ratchet mechanism. Unlocking of the locking mechanism enables ready disassembly of the assembly for cleaning and component sterilization.

13 Claims, 7 Drawing Sheets

U.S. PATENT DOCUMENTS

| | | |
|---|---|---|
| 6,260,446 B1 | 7/2001 | Hu |
| 6,299,616 B1 | 10/2001 | Beger |
| 6,305,248 B1 | 10/2001 | Rowlay |
| 6,639,137 B2 * | 10/2003 | Lauer .......................... 84/453 |
| 6,658,970 B2 | 12/2003 | Shiao |
| 6,679,143 B2 * | 1/2004 | Rastegar et al. ............... 81/466 |
| 6,739,224 B1 * | 5/2004 | Wershe ........................ 81/437 |
| 6,817,458 B1 | 11/2004 | Gauthier et al. |
| 6,978,700 B2 * | 12/2005 | Chen ............................. 81/60 |
| 6,997,087 B2 * | 2/2006 | Rastegar et al. ............... 81/466 |
| 2001/0020403 A1 * | 9/2001 | Jarrett .......................... 81/60 |
| 2002/0102143 A1 | 8/2002 | Huang |

\* cited by examiner

DETACHABLE SURGICAL RATCHET

BACKGROUND OF THE INVENTION

This invention relates to drivers for rotary surgical cutting tools, and, more particularly, to drivers used in maxillo-facial, neuro, dental, trauma and orthopedic surgery, including reamer drivers.

Surgical ratchets are complicated mechanical devices which have crevices and recesses that, heretofore, have been difficult, if not almost impossible to clean with ease. Devices that are not properly cleaned and sterilized run the risk of disease transfer from patient to patient following the emergence of certain "prions" that are not killed by normal hospital sterilisation and need to be physically removed by washing/rinsing. For this reason, in the prior art, ratchet mechanisms have be hermetically sealed to prevent contamination. However, the seals are not 100% reliable.

What is needed therefore is a surgical ratchet that is easily disassemblable for cleaning, so as to better ensure sterilization.

SUMMARY OF THE INVENTION

A surgical ratchet assembly includes a handle, a driver, a ratcheting mechanism and a locking mechanism. The driver is received within the handle in a rotatable relationship with respect thereto. The ratcheting mechanism is interposed between the handle and the driver. The ratcheting mechanism includes pawls which can be selectively locked out of engagement with a toothed hub via a selector. A locking mechanism releasably holds the handle to the ratchet mechanism. Unlocking of the locking mechanism enables ready disassembly of the assembly for cleaning and component sterilization.

Although the term "driver" is used herein, this terms is meant to encompass drills, taps, guide pins, screwdrivers (for example, straight, cross-head, Allen key and Torx), reamer drivers, and wire introducers and any tool to which rotation and torque need be applied.

In another feature, the selector includes a position in which both pawls are in an engaged position, thus locking the ratchet mechanism against free movement in either direction.

In another feature, the selector includes a position in which both pawls are in a released, nonengaged position, disengaging the ratchet mechanism, thus permitting free motion in either direction.

An object of the invention is to provide a surgical ratchet that is readily disassembled for cleaning and sterilization.

Another object of the invention is to provide a reliable ratchet that is easy to operate.

DETAILED DESCRIPTION OF THE PREFERRED EMBODIMENT

Figure 1A:
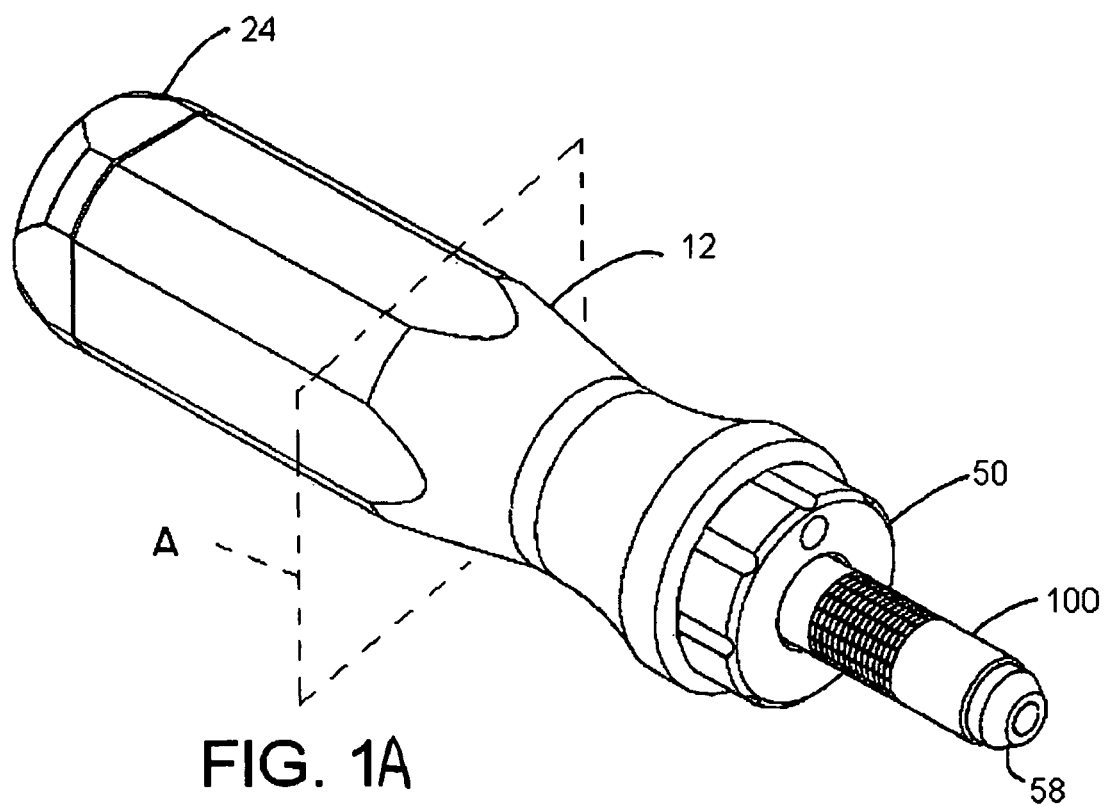
FIG. 1 is a perspective view of the ratchet of the invention.
Figure 1B:
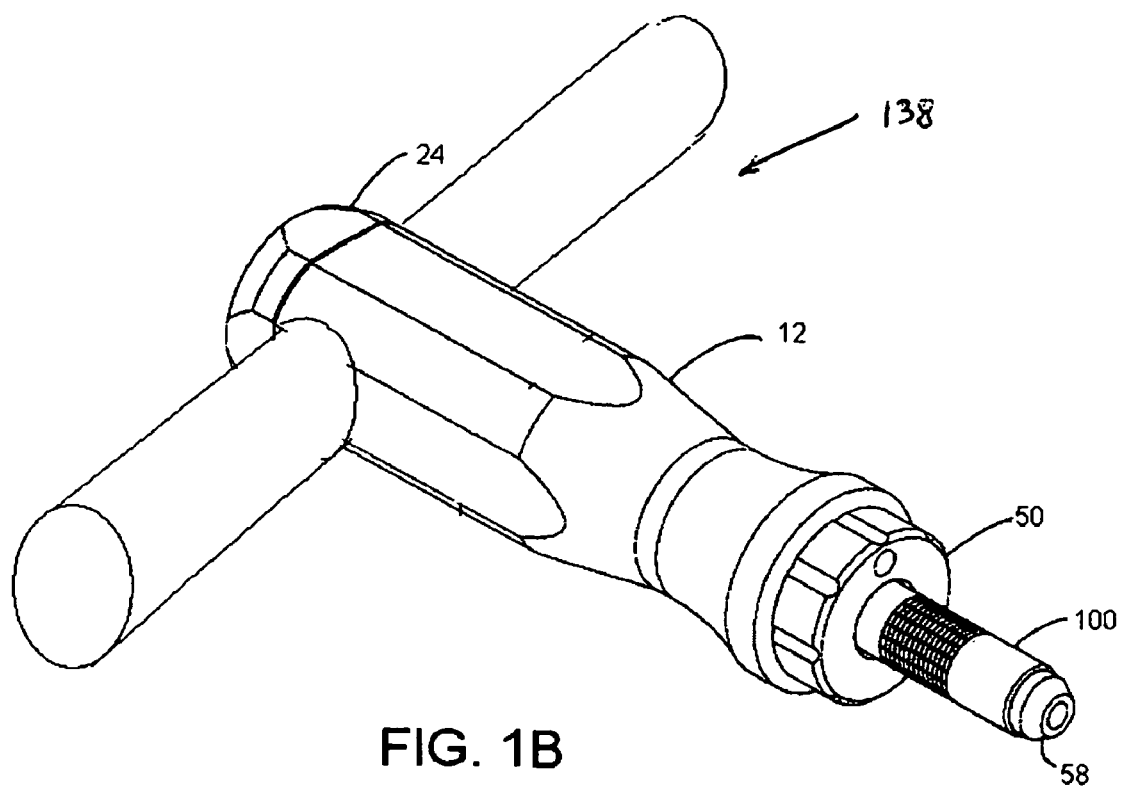
Figure 2A:
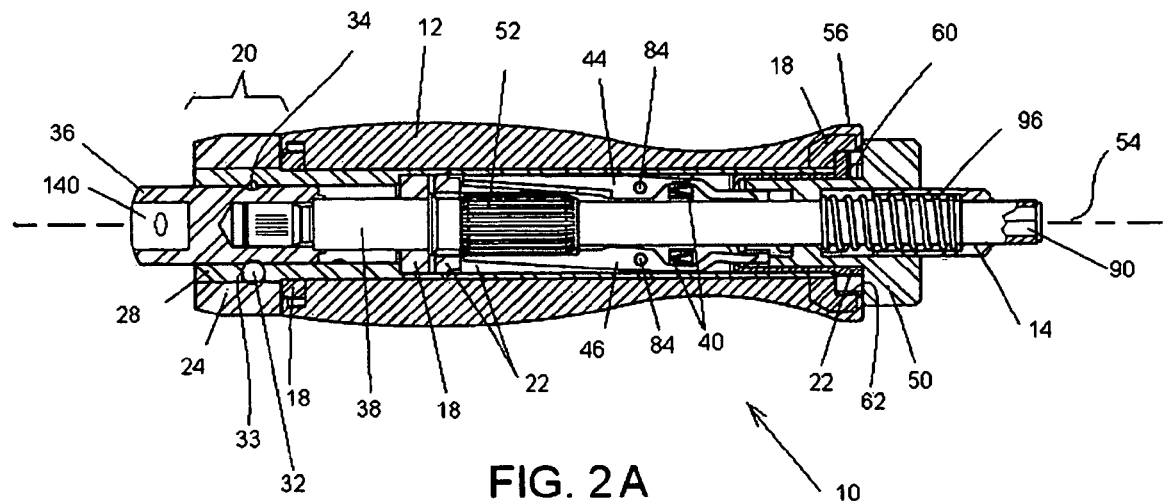
FIG. 2A is cross sectional view of the ratchet of the invention.
Figure 2B:
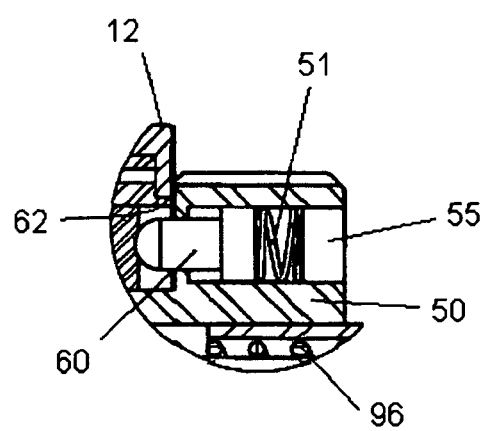
FIG. 2B is a cross sectional detail of the upper right corner of the ratchet of FIG. 2A.
Figure 3:
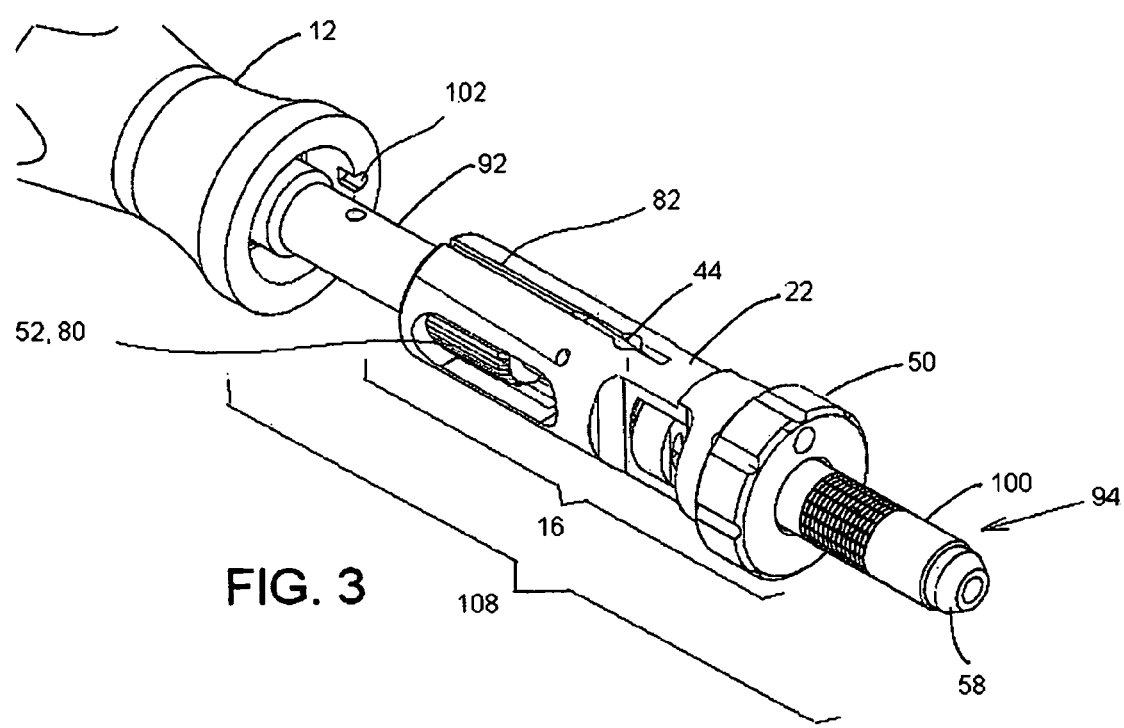
FIG. 3 is a partially disassembled view of the ratchet of the invention.

In a preferred embodiment, as shown in FIGS. 1 to 3, a surgical ratchet assembly 10 includes a handle 12, a driver 14, a ratcheting mechanism 16 and a locking mechanism 20. The driver 14 is received within the handle 12 in a rotatable relationship with respect thereto. The ratcheting mechanism 16 is interposed between the handle 12 and the driver 14. The locking mechanism 20 releasably holds the handle 12 to the ratchet mechanism 16. Unlocking of the locking mechanism 20 enables ready disassembly of the assembly 10 for cleaning and component sterilization.

The locking mechanism 20 includes a ring 24 which is mounted over an annular surface on a hub 28 non-rotatably affixed to the handle 12. The ring 24 has an external surface which is preferrably polygonal in cross section in order to provide a grip to facilitate operation by the user. The ring 24 is locked by a retainer ring, set screw or other fastener (not shown) so as to be restrained to axially rotate about the handle 12. The inner surface of the ring 24 includes equally spaced apart balls 32 restrained in recesses 33 of the hub 28. The balls 32 are selectively biased into or out of an annular recess 34 in the annular rearward end 36 of the driver 14.

The driver 14 includes the end 36 affixed to a central shaft 38 on which is formed a toothed hub 52. The end 36 is formed of a material that can withstand impaction of a mallet and effectively transmit the forces so input through the driver 14 to the object being impacted.

Figure 4:
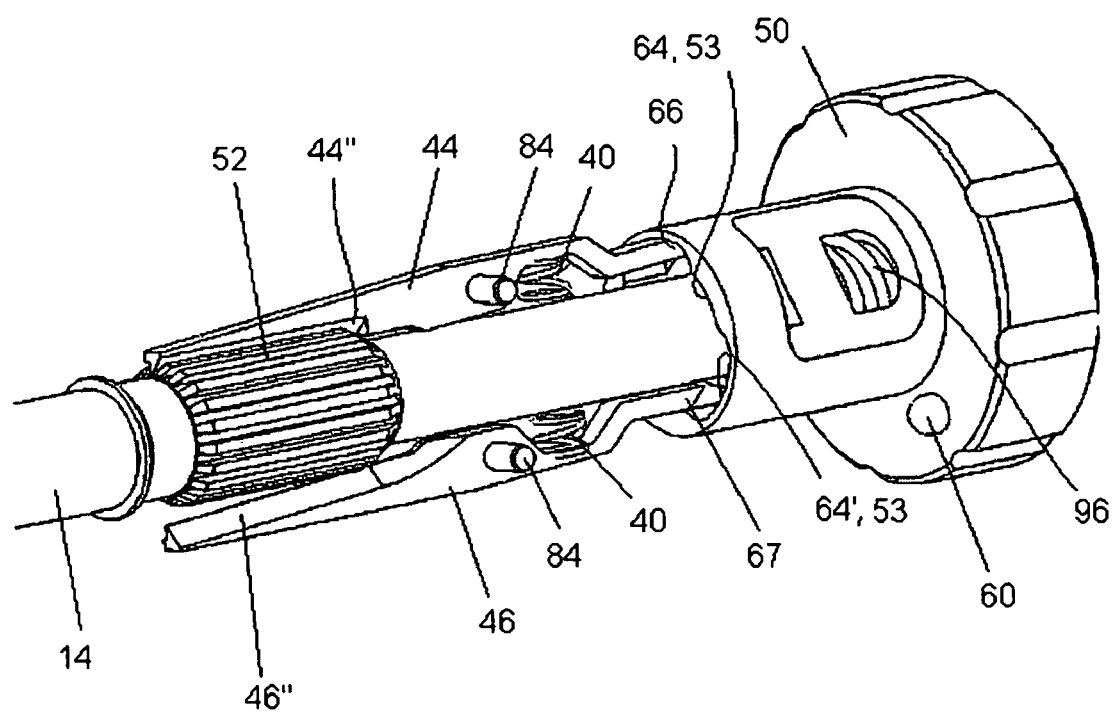
FIG. 4 is a perspective, particlly disassembled view of the ratchet of the invention.
Figure 5:
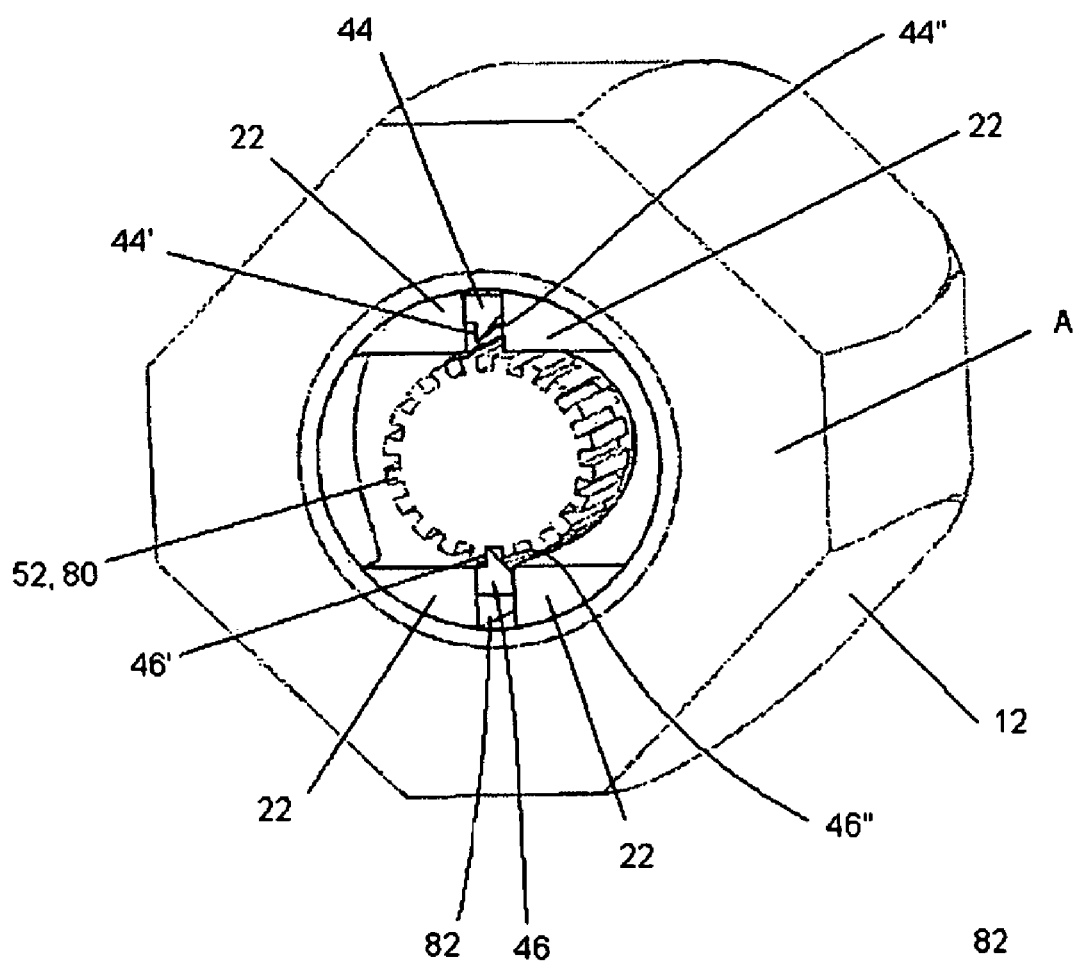
FIG. 5 is a perspective, cross sectional view taken along plane A of FIG. 1, showing the components of the ratchet mechanism of the invention.

Referring now to FIGS. 4-5, the ratcheting mechanism 16 is made up of an internal housing 22, left and right hand pawls 44, 46, a selector 50, the toothed hub 52, biasing springs 40, and cam portions 53.

The selector 50 rotates about the axis 54 of the driver 14, about an end 56 of the handle 12, and selectively locks, via a spring detent 60 (best shown in FIG. 2B) in one of two recesses 62 in the internal housing 22, at two extreme positions. The spring detent 60 is made up of a plunger 60, spring 51, enclosed by a plug 55. The selector 50 has an internal surface 64 having cam portions 53 (referring in particular to FIG. 4, adjacent the right ends 66, 67 of the pawls 44, 46, respectively) which selectively engage the end of either the left or right hand pawls. In toothed hub 52, and therefore the driver 14, is keyed against rotation relative to the handle 12 and therefore moves with the handle. In other words, when the handle 12 is rotated, the toothed hub 52 and driver 14 rotates.

It should be noted that the handle 12 is generally formed of a polymeric material that is comfortable to grip, but which includes inserts 18 to add structural rigidity.

Referring again to FIG. 2A, the pawls 44, 46 are formed so as to engage with the symmetrical, circumferential teeth 80 of the toothed hub 52, thus preventing motion in one direction, while permitting rotation in the opposite rotation. In the present embodiment, the pawls 44, 46 have fingers presenting a flat, locking surface 44', 46' which, when the cam places them in an operational position, engages and therefore blocks a tooth 80 of the toothed hub 52 when the hub is urged in one rotational direction with respect to the handle 12, and an opposing angled surface 44", 46", which does not lockingly engage a tooth of the toothed hub, but enables relative rotation of the pawl and toothed hub, when urged in the opposite direction. The pawls 44, 46 are supported against bending in channels 82 of the housing 22.

The pawls 44, 46 are pivotally mounted in the housing 22 on pins 84 and normally urged into an engaging relationship by springs 40, the cam portions 53 of the selector 50 selectively moves one or the other out of engagement with the toothed hub 52, thus enabling a user to drive the driver 14 in one direction by turning the handle 12, while permitting relative movement of the toothed hub and the pawls when the handle is turned in the other direction. Thus, movement of the selector 50 in one or the other extreme positions allows the user to select a ratcheting direction.

In a mid position, in which there may optionally be a spring detent, the internal surface 64 is at a low point 64', and thus the cam portions 53 of the selector 50 place both pawls 44, 46 in an operational position so as to block rotation in both directions, enabling a functioning just as a normal, non-ratcheting driver.

In another mid position, the cam of the selector 50 optionally moves both pawls 44, 46 out of engagement with the toothed hub 52, thus providing a neutral position in which the handle 12 is free to turn in either direction.

The driver 14 includes a fitting interface 90 on an end of the central shaft 38. The shaft 38 extends from the front to the rearward end of the ratchet 10. The fitting interface 90 interfaces with an AO fitting, a Snyder fitting, or another known fitting 58. A fitting locking mechanism 94 locks the fitting (not shown) into engagement with the driver 14. The fitting locking mechanism 94 includes a locking sleeve 100, axially biased by a spring 96 acting against a recess 94 in the selector 50.

The ratchet 10 enables easy dissassembly for cleaning, which involves the following steps. In a first disassembly step, the locking ring 24 is twisted to an unlocked position. In a second disassembly step, the internal ratchet body 108 (the assembled-together driver 14 and ratchet mechanism 16) is removed for cleaning.

Further, a simple method of assembly is provided which includes the following steps. In a first assembly step, the ratchet body 108 is inserted into the handle 12. In a second assembly step, an alignment pin (not shown) is aligned with a slot 102 in the handle 12 in order that the user properly aligns the ratchet body with the handle. In a third assembly step, the body 108 is pushed into the handle 12 until it can go no further. In a fourth assembly step, the locking ring 24 is then twisted into a locking position. In an optional fifth assembly step, a tool 58 is selected from a kit 150, and inserted into the driver 14. The ratchet assembly 10 is now ready for use.

Figure 6:
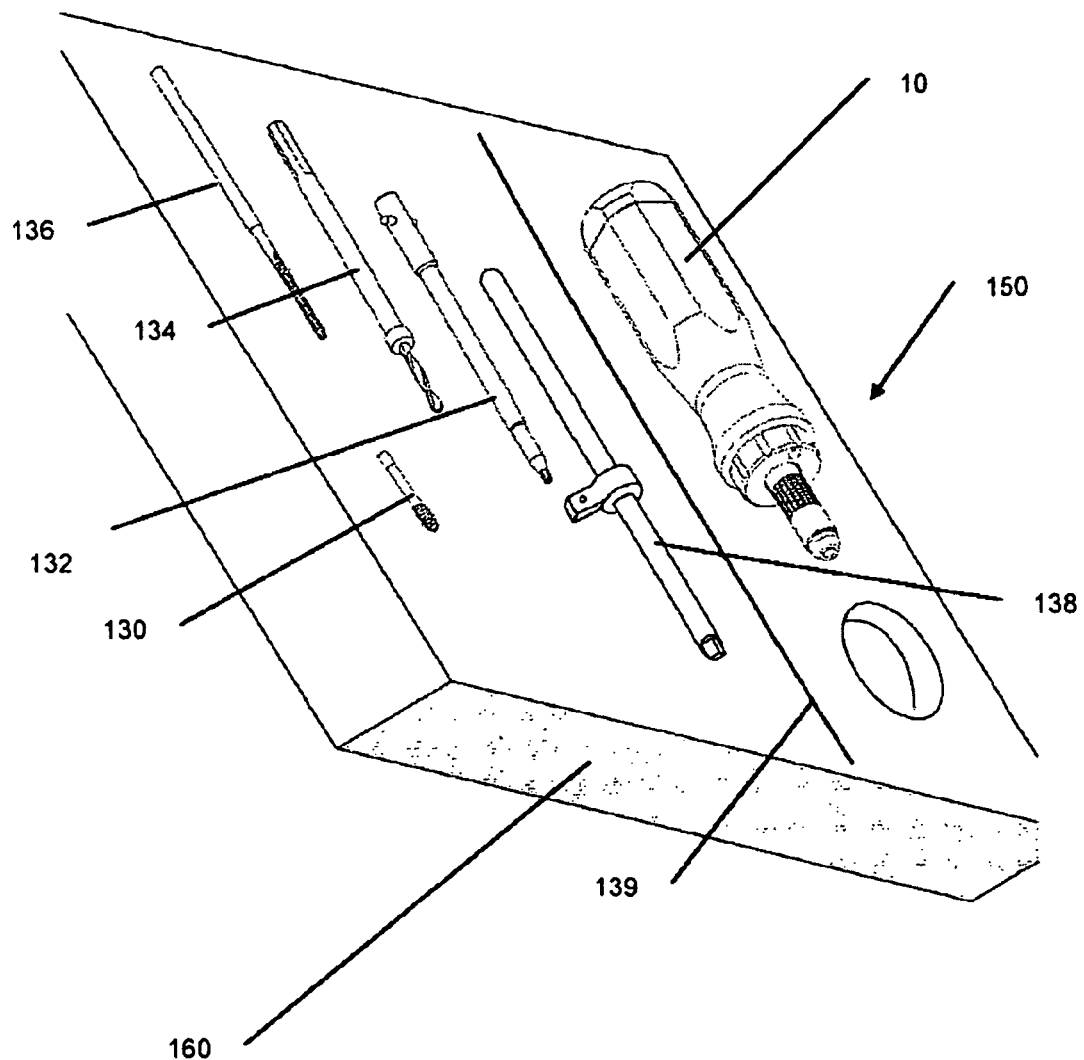
FIG. 6 is a perspective view of a kit of the invention.

Referring now to FIG. 6, the kit 150 is shown, including the ratchet 10, a a tool 130, 132, 134, 136, a T-bar 138 and a guide pin 139. The components of the kit 150 are organized in a case 160 for convenience.

The T-bar 138 includes a square plug drive that mates with the end 36 having a corresponding female socket 140. In this alternate embodiment, the end 36 is either integral with or firmly affixed to the other components of the driver 14 so as to be able to effectively transmit torque therethrough.

In an advantage of the invention, a surgical ratchet is provided that is readily disassembled for cleaning and sterilization.

In another advantage of the invention, a reliable ratchet is provided that is easy to operate.

In another advantage, an assembly method is provided involving only a few simple steps.

In another advantage, a kit is provided which presents the ratchet 10 and related components to the surgeon in a convient, organized fashion.

In another advantage, a T-bar attachment enables increased torque to be transmitted through to the object being driven, by virtue of the large lever arm distance afforded by the T-bar. Convenience is gained because it is not necessary to re-grip the T-bar each time torque is to be input—rather, the ratchet mechanism enables easy and advantageous repositioning.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A surgical ratchet (10) assembly having a handle (10), a driver (14) received within the handle in a rotatable relationship with respect thereto, a ratcheting mechanism (16), and a locking mechanism (20) releasably holding the assembly together, wherein displacing of the locking mechanism to an unlock position moves a locking obstruction (32) out of an obstructing position thereby permitting easy disassembly of the assembly, wherein the locking mechanism (20) comprises a ring (24) rotatable on the handle (12), the ring having a surface selectively biasing a ball (32) into or out of a recess (34) to engage or disengage the locking obstruction (16) to lock or unlock the assembly.

2. The ratchet assembly (10) of claim 1, wherein the locking mechanism (20) comprises a surface against which a user may apply pressure to effectuate a change in interactivity of components in order to engage or disengage the ratchet mechanism (16) to lock or unlock the assembly.

3. The ratchet assembly (10) of claim 1, wherein a selector (50) enables a user to activate, disactivate, or lock the ratcheting mechanism (16).

4. The ratchet assembly (10) of claim 1, wherein the locking mechanism (20) is comprised of a selector (50) having a position in which at least one pawl (44, 46) is in an engaged position, wherein, when the selector is in the engaged position, the at least one pawl locks the ratchet mechanism against free movement in a selected direction.

5. The ratchet assembly (10) of claim 1, wherein the locking mechanism (16) is comprised of a selector (50) having a position in which at least one pawl (44, 46) is in a released position, wherein, when the selector is in the released position, the at least one pawl disengages the ratchet mechanism, thus permitting free motion in either direction.

6. The surgical ratchet assembly 10 of claim 1 wherein a portion of the driver (14) protrudes from an end (36) of the handle (12), thereby presenting an impaction surface enabling the ratchet assembly to be used as an impactor.

7. The ratchet assembly (10) of claim 1, wherein the ratcheting mechanism (16) comprises
  (a) a housing (22) in which left and right hand pawls (44, 46) are pivotably connected and selectively pivotably engageable by a cam selection device (50) for selection of a ratcheting direction; and
  (b) a toothed hub (52) connected, at least indirectly, to the handle.

8. The ratchet assembly (10) of claim 7, wherein the cam selection device (50) comprises a cam having a cam surface (53) against which an end (66, 67) of the at least one pawl (44, 46) rides and wherein relative movement of the cam surface to the end of the at least one pawl causes the pawl to pivot in a prescribed manner.

9. The ratchet assembly (10) of claim 1, wherein an end (66, 67) of the at least one pawl (44, 46) engaging the toothed hub (52) is formed so as to permit relative rotation with respect to the hub in one rotational direction, and to block rotation in the opposite rotational direction.

10. The surgical ratchet (10) assembly of claim 1, wherein the handle (12) is a T-bar (138).

11. The surgical ratchet (10) assembly of claim 1, wherein the handle (12) includes an interface (140) for receiving a T-bar attachment (138).

12. A tool kit (150) for surgical use, the tool kit including at least the following components:
   (a) a surgical ratchet assembly (10) of claim 1;
   (b) at least one tool selected from a group of tools consisting of drills (134), taps (136), guide pins (130), screwdrivers (132), reamer drivers, and wire introducers; and
   (c) a ease (160) for receiving the ratchet and the at least one tool.

13. A surgical ratchet (10) having a handle (12), a driver (14) received within the handle in a rotatable relationship with respect thereto, a ratcheting mechanism (16), and a locking mechanism (20) releasably holding the handle to the ratchet mechanism, wherein displacing the locking mechanism to an unlock position moves a locking obstruction (32) out of an obstructing position thereby permitting easy disassembly,
   wherein the locking mechanism (20) comprises a ring (24) rotatable on the handle, the ring having a surface (53) which selectively biases a ball (32) into or out of a recess (34) to engage or disengage the locking obstruction (32) into or out of an obstructing position thereby permitting locking or easy release of the ratchet mechanism from the handle and ready disassembly of the ratchet mechanism from the handle,
   wherein the ratcheting mechanism (16) comprises
      (a) a housing (22) in which left and right hand pawls (44, 46) are pivotably connected and selectively pivotably engageable by a cam selection device (50) for selection of a ratcheting direction, the cam selection device comprising a cam having a cam surface against which an end of the at least one pawl rides and wherein relative movement of the cam surface to the end of the at least one pawl causes the pawl to pivot in a prescribed manner;
      (b) a toothed hub (52) connected, at least indirectly, to the handle, and
      (c) a selector (50) which has a position in which at least one pawl (44, 46) is in an engaged position, wherein, when the selector is in the engaged position, the at least one pawl locks the ratchet mechanism against free movement in a selected direction, thus enabling a user to activate, disactivate, or lock the ratcheting mechanism.

* * * * *

UNITED STATES PATENT AND TRADEMARK OFFICE
CERTIFICATE OF CORRECTION

| | |
|---|---|
| PATENT NO. | : 7,600,451 B2 |
| APPLICATION NO. | : 10/554044 |
| DATED | : October 13, 2009 |
| INVENTOR(S) | : Andre Lechot and Philippe Fehlbaum |

Page 1 of 1

It is certified that error appears in the above-identified patent and that said Letters Patent is hereby corrected as shown below:

Col. 5, Line 1, Claim 9, delete "of claim 1" and insert -- of claim 8 --.

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,600,451 B2 | Page 1 of 1 |
| APPLICATION NO. | : 10/554044 | |
| DATED | : October 13, 2009 | |
| INVENTOR(S) | : Lechot et al. | |

It is certified that error appears in the above-identified patent and that said Letters Patent is hereby corrected as shown below:

Cover page: add the following at (63):

-- Provisional application No. 60/465,758, filed on April 25, 2003. --

Column 1 after title on line 1, add the following header and paragraph:

-- CROSS REFERENCE TO RELATED APPLICATIONS
This application is the national stage entry of PCT/IB2004/001244, filed April 23, 2004, which claims the benefit of US Provisional Application 60/465,758, filed April 25, 2003. --

Signed and Sealed this
Seventh Day of August, 2012

David J. Kappos
*Director of the United States Patent and Trademark Office*